United States Patent [19]

Cooper et al.

[11] Patent Number: 4,853,392

[45] Date of Patent: Aug. 1, 1989

[54] FUSED 1,4-DIHYDROPYRIDINES AS ANTIALLERGY AND ANTIINFLAMMATORY AGENTS

[75] Inventors: Kelvin Cooper, Deal; Peter E. Cross; Michael J. Fray, both of Canterbury; Kenneth Richardson, Birchington, all of England

[73] Assignee: Pfizer Inc., New York, N.Y.

[21] Appl. No.: 217,584

[22] Filed: Jul. 11, 1988

[30] Foreign Application Priority Data

Jul. 17, 1987 [GB] United Kingdom ............... 8716971

[51] Int. Cl.⁴ ............... A61K 31/47; A61K 31/415; C07D 221/04; C07D 235/04
[52] U.S. Cl. ............... 514/311; 546/170; 546/178; 546/183
[58] Field of Search ............... 546/170, 178, 183; 514/311

[56] References Cited

U.S. PATENT DOCUMENTS 4,677,210  6/1987  Huang ............... 546/170

FOREIGN PATENT DOCUMENTS 2003148  7/1971  Fed. Rep. of Germany ...... 546/170

*Primary Examiner*—Anton H. Sutto
*Assistant Examiner*—Andrew G. Rozycki
*Attorney, Agent, or Firm*—Peter C. Richardson; J. Trevor Lumb; James M. McManus

[57] ABSTRACT

Compounds of the formula

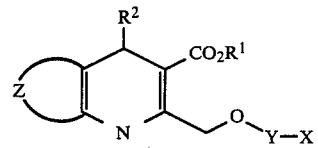

where $R^1$ is lower alkyl, $R^2$ is chlorophenyl, Y is alkylene, X is heterocyclic and Z is a fused ring are useful as antiinflammatory and antiallergy agents.

5 Claims, No Drawings

FUSED 1,4-DIHYDROPYRIDINES AS ANTIALLERGY AND ANTIINFLAMMATORY AGENTS

BACKGROUND OF THE INVENTION

This invention relates to dihydropyridines, specifically to certain 4-aryl-(5,6-bicyclo)-2-(imidazol-1-ylalkoxymethyl)dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-100189.) However the compounds of the present invention are potent and selective antagonists of platelet activating factor and as such they have clinical utility in a quite different area, namely for treating allergic and inflammatory conditions such as asthma and arthritis respectively.

Platelet activating factor (PAF) 1-0-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. For example in vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, which associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic inflammatory and hypersecretory conditions such as asthma, arthritis, rhinitis, bronchitis and uticaria.

In addition to the above, PAF has been implicated as being involved in a number of other medical conditions. Thus in circulatory shock, which is characterized by systemic hypotension, pulmonary hypertension and increased lung vascular permeability, the symptoms can be mimicked by infusion of PAF. This coupled with evidence showing that circulating RAF levels are increased by endotoxin infusion indicate that PAF is a prime mediator in certain forms of shock. Intravenous infusion of PAF at doses of 20–200 pmol $kg^{-1}$ $min^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterized by skin lesions. PAF is pro-inflammatory and has been isolated from lesioned scale of psoriatic patients including PAF has a role in the disease of psoriasis. And finally, increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and in guinea pig hearts it induces regional shunting and ischaemia. In addition PAF has been shown to initiate thrombus formation in a mesenteric artery preparation, both when administered exogenously and when released endogenously. More recently PAF has been shown to play a role in brain ischaemia in animal models of stroke. Thus the compounds of the invention, by virtue of their ability to antagonise the actions of PAF, could be of value in the treatment of any of these conditions.

Our copending published European Patent Application EP 258033 and unpublished European Patent Application 87.309674.7 disclose 4-aryl-5-carbamoyl-1,4-dihydropyridines as PAF antagonists.

SUMMARY OF THE INVENTION

According to the present invention there are provided compounds of the formula:

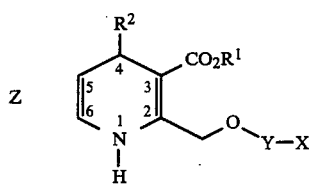

and their pharmaceutically acceptable salts;
wherein $R^1$ is alkyl of one to three carbon atoms; $R^2$ is 2-chlorophenyl; Y is alkylene of two to five carbon atoms having at least two carbon atoms in the chain linking X and the oxygen atom; X is 2-alkylimidazol-1-yl said alkyl having one to four carbon atoms, 2,4,5-trimethylimidazol-1-yl or 2-methylbenzimidazol-1-yl; and Z is

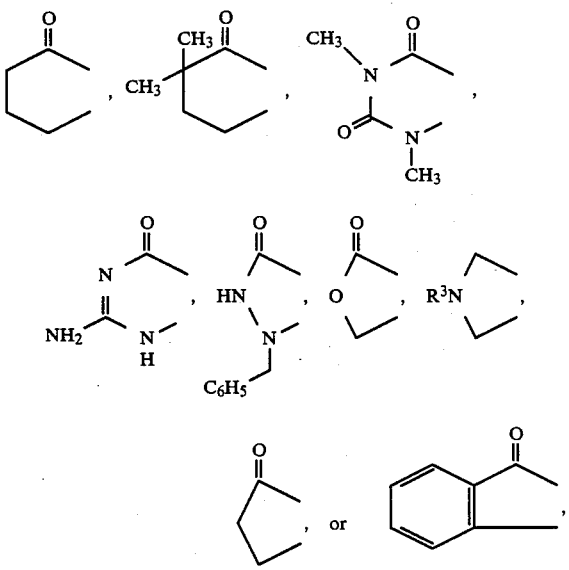

where $R^3$ is benzyl or cyclohexyl.

A preferred group of compounds are those where $R^1$ is ethyl, $R^2$ is 2-chlorophenyl and Y is ethylene. Especially preferred in this group is the compound where X is 2-methylbenzimidazol-1-yl and Z is

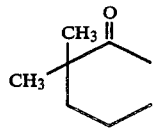

and where X is 2,4,5-trimethylimidazol-1-yl and Z is

where $R^3$ is benzyl.

Also part of the present invention is a method for treating an inflammatory or allergic reaction in a mammal which comprises administering to said mammal an antiinflammatory or antiallergic effective amount of a compound of formula I.

The present invention also includes a pharmaceutical composition comprising a unit dosage form of a compound of formula I together with a pharmaceutically acceptable carrier or diluent.

As one skilled in the art will recognize, when Z is

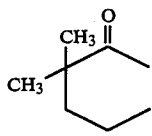

the fused compound is of the structure

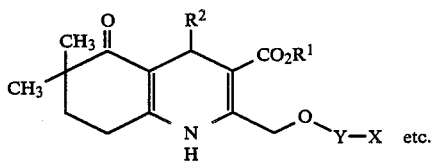

The compounds of the formula (I) containing at least one asymmetric centres will exists as one or more pairs of enantiomers, and such pairs or individual isomers may be separable by physical methods, e.g. by fractional crystallisation or chromatography of the parent compounds or of a suitable salt or derivatives thereof. The invention includes all the enantiomers whether separated or not.

The pharmaceutically acceptable acid addition salts of the compounds of the formula (I) are those formed from acids whch form non-toxic acid addition salts, for example the hydrochloride, hydrobromide, sulphate or bisulphate, phosphate or acid phosphate, acetate, citrate, fumarate, gluconate, lactate, maleate, succinate, tartrate, methane sulphonate and benzenesulphonate.

DETAILED DESCRIPTION OF THE INVENTION

The compounds of formula I may be obtained by a number of different processes in accordance with the invention:

(a) In one process, the compounds are obtained by the Hantzsch synthesis, according to the following reaction scheme:

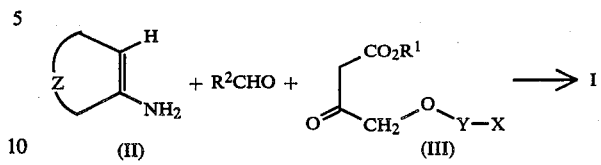

wherein $R^1$, $R^2$, Y, X and Z are as previously defined.

In a typical procedure, the ketoester (III) and aldehyde are heated under reflux, in a suitable organic solvent, e.g. a $C_1$–$C_4$ alkanol such as ethanol, with the compound of formula (II) for up to 16 hours. The product of the formula (I) can then be isolated and purified by conventional procedures, for example by partition, recrystallization or chromatography.

The keto esters (III) are either known compounds or can be prepared by methods analogous to those of the prior art, such as the method described in European patent 100189 which is essentially the method of Troostwijk and Kellogg, J. C. S. Chem. Comm., 1977, page 932 or as described in the Preparations given hereafter.

Similarly the compounds of formula (II) are either known compounds or can be prepared by conventional procedures.

The aldehydes $R^2$CHO are either known or can be prepared by known methods in accordance with literature precedents.

(b) In an alternative procedure, the compounds of formula (I) in which Z is

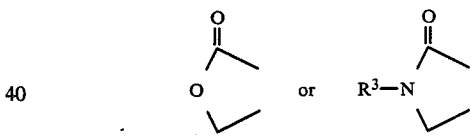

where $R^3$ is H, $C_1$–$C_4$ alkyl, $C_3$–$C_7$ cycloalkyl or aryl($C_1$–$C_4$)alkyl, are prepared from a compound of formula (IV):

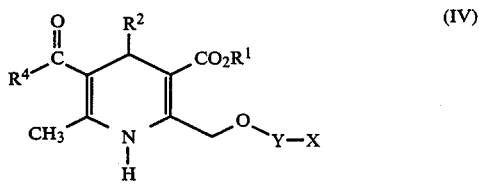

wherein $R^4$ is $C_1$–$C_6$ alkyl (such as methyl) or aryl(-$C_1$–$C_4$)alkyl by stirring at 0° C. under nitrogen with pyridinium bromide perbromide and pyridine in chloroform for about 1 hour, optionally followed by addition of the appropriate amine $R^3NH_2$, e.g. cyclohexylamine, benzylamine or ammonia. The mixture is then refluxed for up to 3 hours. The product of formula (I) can then be isolated and purified by conventional procedures, for example partition, recrystallisation or by chromatography.

The starting materials of formula (IV) are prepared by conventional methods, for example by the Hantzsch synthesis described under (a).

(c) In a further alternative procedure, the compounds of formula (I) in which Z is:

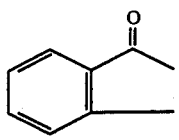

may be prepared by reaction of a compound of formula V:

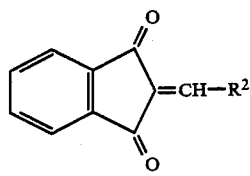

(V)

with the compound of formula (III) from (a) in the presence of an ammonium salt, for example by refluxing in the presence of ammonium acetate and glacial acetic acid for about 5 minutes. The product is then neutralized and isolated and purified by conventional procedures, e.g. by chromatography.

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated for two minutes at 37° C. in a Paton aggregometer with stirring, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propanolol (5 mg/kg) in 0.9% w/v sodium chloride is injected (0.2 ml) via a tail vein into mice. The compounds under test are either injected into the tail vein immediately prior to the PAF/propanolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-included bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the test repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2–1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with this age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes compound of the formula (I), or a pharmaceutically acceptable salt thereof, for use in medicine, in particular in the treatment of allergic and inflammatory conditions in a human being.

The preparation of the compounds of the invention is further illustrated by the following Examples.

EXAMPLE 1

4-(2-Chlorophenyl)-3-ethoxycarbonyl-2-[2-(2-n-propylimidazol-1-yl)propoxymethyl]-1,4,5,6,7,8-hexahydro-5-oxoquinoline Ethyl 4-[2-(2-n-propylimidazol-1-yl)propoxy]-3-ketobutanoate (590 mg), 3-aminocyclohex-2-enone (220 mg) and 2-chlorobenzaldehyde (281 mg) were stirred in refluxing ethanol (8 ml) for 8 hours. The solvent was removed under reduced pressure. The crude product was chromatographed over silica eluting with a mixture of diethylamine and ethyl acetate (1:49). The solvents were removed in vacuo and the residue rechromatographed over silica eluting with a mixture of methanol and ethyl acetate [1:9]. The solvents were removed in vacuo. The resulting foam was stirred in ether overnight, the solid filtered and dried in vacuo yielding the title compound as a white solid 220 mg (22%). M.p. 127°–131° C.

Analysis %:
Found: C,65.27; H,6.82; N,8.05.
$C_{28}H_{34}ClN_3O_4$ requires: C,65.67; H,6.69; N,8.21.

EXAMPLES 2–7

The following compounds were made by the method of Example 1 using as starting materials 3-aminocyclohex-2-enone, 2-chlorobenzaldehyde and the appropriately substituted alkyl ketobutanoate:

| Example No. | $R^1$ | —Y—X | m.p. °C. | C | H | N |
|---|---|---|---|---|---|---|
| 2 | —$CH_2CH_3$ | —$CH_2CH$(—$CH_3$)—N⟨2,4,5-trimethylimidazol-1-yl⟩ | 163–166 | 64.28 (65.54 | 6.78 6.77 | 8.17 8.06)# |
| 3 | —$CH_2CH_3$ | —$CH_2C$($CH_3$)$_2$—N⟨2-methylimidazol-1-yl⟩ | 135–137 | 64.37 (63.95 | 6.39 6.56 | 8.44 8.29)# |
| 4 | —$CH_2CH_3$ | —$CH_2CH_2$—N⟨2-methylbenzimidazol-1-yl⟩ | 155–160 | 66.99 (66.97 | 5.77 5.82 | 8.15 8.08) |
| 5 | —$CH_2CH_3$ | —$CH_2C$($CH_3$)$_2$—N⟨2-methylbenzimidazol-1-yl⟩ | 187–189 | 67.38 (67.38 | 6.41 6.29 | 7.63 7.60)* |
| 6 | —$CH_3$ | —$CH_2CH_2$—N⟨2,4,5-trimethylimidazol-1-yl⟩ | 136–138 | 64.24 (64.46 | 6.42 6.19 | 8.34 8.68) |
| 7 | —$CH_2CH_3$ | —$CH_2CH_2$—N⟨2,4,5-trimethylimidazol-1-yl⟩ | 153–155 | 65.16 (65.06 | 6.52 6.42 | 8.28 8.43) |

Calculated for ½ $H_2O$
*Calculated for ¼ $H_2O$

EXAMPLE 8

5-(2-Chlorophenyl)-6-methoxycarbonyl-1,3-dimethyl-7-[2-(2,4,5-trimethylimidazol-1-yl)ethoxymethyl]-1,2,3,4,5,8-hexahydro-2,4-dioxopyrido[2,3-d]pyrimidine The title compound (210 mg) was prepared from 2-chlorobenzaldehyde (1.4 g), 6-amino-1,3-dimethyl-2,4-dioxopyrimidine (1.55 g) and methyl 4-[2-(2,4,5- trimethylimidazol-1-yl)ethoxy]3-oxobutanoate (2.68 g) by the method of Exmaple 1. M.p. 226°–228° C.

Analysis %:
Found: C,57.36; H,5.48; N,12.60. Calculated for $C_{26}H_{30}ClN_5O_5.H_2O$: C,57.14: H,5.86; N,12.82.

EXAMPLE 9

The 6-ethoxycarbonyl analogue of Example 8 (950 mg) was prepared from 2-chlorobenzaldehyde (1.69 g), 6-amino-1,3-dimethyl-2,4-dioxopyrimidine (1.87 g) and ethyl 4-[2-(2,4,5-trimethylimidazol-1-yl)ethoxy]-3-oxobutanoate (3.4 g) by the method of Example 1. M.p. 169°–171° C.

Analysis %:
Found: C,59.34; H,5.87; N,12.73; Calculated for $C_{27}H_{32}ClN_5O_5$: C,59.76; H,5.90; N,12.91.

EXAMPLE 10

5-(2-Chlorophenyl)-6-methoxycarbonyl-1,3-dimethyl-7-[2-(2,4,5-trimethylimidazol-1-yl)-propoxymethyl]-1,2,3,4,5,8-hexahydro-2,4-dioxopyrido-[2,3-d]pyrimidine The title compound (150 mg) was prepared from 2-chlorobenzaldehyde (747 mg), 6-amino-1,3-dimethyl-2,4-dioxopyrimidine (824 mg) and methyl 4-[2-(2,4,5-trimethylimidazol-1-yl)propoxyl]3-oxobutanoate (1.5 g) by the method of Example 1. M.p. 180°–182° C.

Analysis %: Found: C,58.49; H,5.86; N,12.50; Calculated for $C_{27}H_{32}ClN_5O_5.\frac{1}{2}H_2O$: C,58.80; H,5.98; N,12.70.

EXAMPLE 11

2-Amino-5-(2-chlorophenyl)-6-methoxycarbonyl-7-[2-(2,4,5-trimethylimidazol-1-yl)ethoxymethyl]-1,4,5,8-tetrahydro-4-oxopyrido[2,3-d]pyrimidine The title compound (110 mg) was prepared from 2-chlorobenzaldehyde (1.05 g), 2,4-diamino-6-hydroxypyrimidine (1.07 g) and methyl 4-[2-(2,4,5-trimethylimidazol-1-yl)ethoxy]-3-oxobutanoate (2.0 g) by the method of Example 1. M.p. 225°–227° C.

Analysis % Found: C,57.16; H,5.32; N,16.58 Calculated for $C_{24}H_{27}ClN_6O_4.\frac{1}{4}CH_3OH$: C,57.30; H,5.52; N,16.56.

EXAMPLE 12

1-Benzyl-4-(2-chlorophenyl)-5-methoxycarbonyl-6-[2-(2,4,5-trimethylimidazol-1-yl)ethoxymethyl]-1H-2,3,4,7-tetrahydro-3-oxopyrazolo[3,4-b]pyridine 1-Benzyl-5-amino-2-pyrazolin-3-one (1.44 g), 2-chlorobenzaldehyde (1.08 g) and methyl 4-[2-(2,4,5-trimethylimidazol-1-yl)ethoxy]-3-oxobutanoate (2.05 g) were heated in refluxing ethanol for sixteen hours, cooled and the resultant precipiate separated by filtration to give the title compound (2.0 g) as a colourless solid. M.p. 178-180° C.

Analysis %: Found: C,63,67; H,5.64; N,12.57; Calculated for $C_{30}H_{32}ClN_5O_4$: C,64.06; H,5.69; N,12.45.

EXAMPLE 13

4-(2-Chlorophenyl)-3-ethoxycarbonyl-6,6-dimethyl-2-[2-(2-methylbenzimidazol-1-yl)ethoxymethyl]-1,4,5,6,7,8-hexahydro-5-oxoquinoline The title compound (63 mg) was prepared from 2-chlorobenzaldehyde (202 mg), 3-amino-6,6-dimethyl-2-cyclohexene-1-one (200 mg) and ethyl 4-[2-(2-methyl-benzimidazol-1-yl)ethoxy]-3-oxobutanoate (304 mg) by the method of Example 1. M.p. 118°–120° C.

Analysis %: Found: C,64.71; H,6.15; N,7.07; Calculated for $C_{31}H_{34}ClN_3O_4.\frac{1}{4}H_2O$: C,64.69; H,6.43; N,7.30.

EXAMPLE 14

4-(2-Chlorophenyl)-3-ethoxycarbonyl-2-[2-(2,4,5-trimethylimidazol-1-yl)ethoxymethyl]-1,4,5,7-tetrahydro-5-oxofuro[3,4-b]pyridine A solution of 4-(2-chlorophenyl)-3-ethoxycarbonyl-5-methoxycarbonyl-6-methyl-2-[2-(2,4,5-trimethylimidazol-1-yl)ethoxymethyl]-1,4-dihydropyridine (3.0 g) in chloroform (50 cm³) stirred at 0° C. under $N_2$ was treated with pyridine (790 mg) followed by pyridinium bromide perbromide (2.1 g) in portions over five minutes and the mixture stirred at 0° C. for one hour and then heated at reflux temperature for three hours. The solution was cooled, washed with 2N hydrochloric acid (2×50 cm³) and brine (50 cm³), dried over $MgSO_4$, filtered and evaporated to dryness. The residue was purified by silica-gel column chromatography eluting with diethylamine/ethyl acetate (1:9). The appropriate fractions were evaporated to dryness and taken up in ethyl acetate (25 cm³) from which the title compound crystallised as a colourless solid (440 mg). M.p. 215°–217° C.

Analysis %: Found: C,61.61; H,5.84; N,8.55. Calculated for $C_{25}H_{28}ClN_3O_5$: C,61.73; H,5.76; N,8.64.

EXAMPLE 15

4-(2-Chlorophenyl)-6-cyclohexyl-3-ethoxycarbonyl-2-[2-(2,4,5-trimethylimidazol-1-yl)ethoxymethyl]-6H-1,4,5,7-tetrahydro-5-oxopyrrolo[3,4-b]pyridine A solution of 4-(2-chlorophenyl)-3-ethoxycarbonyl-5-methoxycarbonyl-6-methyl-2-[2-(2,4,5-trimethylimidazol-1-yl)ethoxymethyl]-1,4-dihydropyridine (3.0 g) and pyridine (807 μl) in chloroform (40 cm³) stirred at 0° C. under $N_2$ was treated with pyridinim bromide perbromide (2.1 g) in portions over five minutes and the mixture stirred at 0° C. for one hour. Cyclohexylamine (5 cm³) was added and the mixture warmed at reflux temperature for one hour, cooled and evaporated to dryness. The residue was taken up in ethanol (15 cm³) and treated with 2N potassium hydroxide solution (1.25 cm³). The mixture was stirred overnight, evaporated to dryness and the residue taken up in dichloromethane, (50 cm³) washed with 2N hydrochloric acid (50 cm³), saturated sodium hydrogen carbonate (50 cm³) and brine (50 cm³), dried over $MgSO_4$, filtered and evaporated to dryness. The residue was purified by silica gel column chromatography eluting with diethylamine/ethyl acetate (1:9) to give the title compound (155 mg). M.p. 107°–109° C.

Analysis %: Found: C,63.94; H,7.02; N,9.28; Calculated for $C_{31}H_{39}ClN_4O_4.H_2O$: C,63.58; H,7.00; N,9.57.

EXAMPLE 16

6-Benzyl-4-(2-chlorophenyl)-3-ethoxycarbonyl-2-[2-(2,4,5-trimethylimidazol-1-yl)ethoxymethyl]-6H-1,4,5,7-tetrahydro-5-oxopyrrolo[3,4-b]pyridine The title compound (1.1 g) was prepared by the method of Example 15 but with benzylamine (5 cm³) replacing cyclohexylamine. M.p. 104°–106° C.

Analysis %: Found: C,66.24; H,6.19; N,9.52; Calculated for C$_{32}$H$_{35}$ClN$_4$O$_4$.¼H$_2$O: C,66.20; H,6.12; N,9.65.

EXAMPLE 17

4-(2-Chlorophenyl)-3-ethoxycarbonyl-2-[2-(2,4,5-trimethylimidazol-1-yl)ethoxymethyl]-6H-1,4,5,7-tetrahydro-5-oxopyrrolo[3,4-b]pyridine The title compound (200 mg) was prepared by the method of Example 15 but with the passage of ammonia gas replacing addition of cyclohexlamine. M.p. 212°–215° C.

Analysis %: Found: C,61.74; H,6.21; N,11.53; Calculated for C$_{25}$H$_{29}$ClN$_4$O$_4$: C,61.85; H,5.98; N,11.55.

EXAMPLE 18

4-(2-Chlorophenyl)-3-ethoxycarbonyl-2-[2-(2,4,5-trimethylimidazol-1-yl)ethoxymethyl]-5H-1,4,6,7-tetrahydro-5-oxocyclopenta[b]pyridine The title compound (120 mg) was prepared from 1-amino-1-cyclopentane-3-one (970 mg); 2-chlorobenzaldehyde (1.40 g) and ethyl 4-[2-(2,4,5-trimethylimidazol-1-yl)ethoxy-3-oxobutanoate (2.82 g) by the method of Example 1. M.p. 178°–180° C.

Analysis %: Found: C,63.30; H,6.03; N,8.17; Calculated for C$_{26}$H$_{30}$ClN$_3$O$_4$.1/2H$_2$O: C,63.28; H,6.28; N,8.52.

EXAMPLE 19

4-(2-Chlorophenyl)-3-ethoxycarbonyl-2-[2-(2-methylbenzimidazol-1-yl)ethoxymethyl]-1H-1,4-dihydro-5-oxoindeno[1,2-b]pyridine A solution of 2-(2-chlorobenzylidene)-1,3-dioxoindane (600 mg), ethyl 4-[2-(2-methylbenzimidazol-1-yl)ethoxy]-3-oxobutanoate (678 mg) and ammonium acetate (1.71 g) in glacial acetic acid (5 cm$^3$) was heated at reflux temperature for five minutes, neutralised with 2N potassium hydroxide and extracted with dichloromethane (2×50 cm$^3$). The combined organic extracts were washed with 2N hydrochloric acid (50 cm$^3$). Saturated sodium hydrogen carbonate (50 cm$^3$) and brine (50 cm$^3$), dried (MgSO$_4$) and evaporated to dryness. The residue was purified by silica-gel column chromatography eluting with diethylamine/ethyl acetate (1:9) to give the title compound (400 mg) as a red solid. M.p. 174°–176° C.

Analysis %: Found: C,69.04; H,5.13; N,7.40; Calculated for C$_{32}$H$_{28}$ClN$_3$O$_4$: C,69.31; H,5.05; N,7.58.

The following Preparations illustrate the preparation of certain starting materials used in the previous Examples.

PREPARATION 1

2-(2-Propylimidazol-1-yl)propan-1-ol

1(a) Ethyl-2-(2-propylimidazol-1-yl)propanoate

2-Propylimidazole (5.5 g), ethyl 2-bromopropionate (9.95 g) and potassium carbonate (12.4 g) were stirred in refluxing acetonitrile (100 ml) for 72 hours. The suspension was allowed to cool, filtered and the solvent removed under reduced pressure, yielding the title compound as an off-white foam, 9.2 g [88%].

1(b) 2-(2-Propylimidazol-1-yl)propan-1-ol

Lithium aluminum hydride (2.5 g) was suspended in tetrahydrofuran (40 ml). Ethyl 2-(2-propylimidazol-1-yl)propanate [9.2 g] in tetrahydrofuran (40 ml) was added with stirring at 0° C. The reaction was refluxed for 3 hours, cooled to 0° C., water (3 ml) was added dropwise followed by 15% sodium hydroxide (3 ml) and a further portion of water (9 ml). The suspension was filtered through solka-flok and the solvent removed under reduced pressure. Dichloromethane (50 ml) was added, the organic phase washed with brine (25 ml) dried over magnesium sulphate and the solvent removed under reduced pressure yielding the title compound as a white foam 5.4 g (67%).

N.m.r. (CDCl$_3$) 0.98 (t, J=6Hz, 3H); 1.42 (d, J=6Hz, 3H); 1.73 (q, J=6Hz, 2H); 2.66 (m,2H); 3.74 (m, 2H); 4.29 (q, J=6Hz, 1H); 6.87 (d, J=8Hz, 1H); 6.90 (d, J=8Hz, 1H).

PREPARATION 2

2-(2-Methylbenzimidazol-1-yl)-2-methylpropanol 2(a) 2-(1,1-dimethyl-2-hydroxyethyl)aminoaniline 2-(1,1-dimethyl-2-hydroxyethyl)aminonitrobenzene (10 g) in ethanol (200 ml) was hydrogenated at 50 p.s.i. (345 kPa) over 5% Pd/C (0.5 g) for 2 hours. The catalyst was filtered off and the solvent removed under reduced pressure yielding the title compound as a yellow foam 8.4 g (98%).

N.m.r. (CDCl$_3$) 1.26 (s, 6H); 3.40 (s, 2H); 6.80 (m, 2H); 6.80 (m, 2H); 6.98 (m, 2H).

2(b) 2-(2-Methylbenzimidazol-1-yl)-2-methylpropanol

A mixture of 2-(1,1-dimethyl-2-hydroxyethyl)aminoaniline (from Preparation 2(a)) (8.4 g), acetic acid [4.2 g], and 4N hydrochloric acid [50 ml] were refluxed for 30 hours. The reaction was cooled and neutralised with concentrated aqueous ammonia. The solution was extracted with a mixture of tetrahydrofuran (1 part) and dichloromethane (3 parts) (3×100 ml). The organic phases were combined, dried over magnesium sulphate and the solvent removed under reduced pressure. The crude product was recrystallised from ethyl acetate yielding the title compound as a white solid 3.8 g (40%), m.p. 180°–181° C.

Analysis %: Found: C,70.67; H,7.91; N,13.75; Calculated for: C,70.59; H,7.84; N,13.72.

PREPARATION 3

Ethyl 4-[2-(2-propylimidazol-1-yl)propoxyl]-3-ketobutanoate

Sodium hydride (80% dispersion in oil) (1.76 g) was suspended in dry tetrahydrofuran (40 ml).

2-(2-propylimidazol-1-yl)propan-1-ol (from Preparation 1 above) (5.4 g) was added and the suspension was sonicated until there was no further gas evolution. Ethyl-4-chloroacetoacetate (4.83 g) in tetrahydrofuran (10 ml) was added over 5 minutes with sonication and sonication continued at 25°–35° C. for a further 4 hours. The suspension was poured into 2N hydrochloric acid (30 ml) and the tetrahydrofuran removed under reduced pressure. The aqueous solution was washed with toluene (30 ml) and then neutralised with potassium carbonate. The aqueous solution was extracted with dichloromethane (3×100 ml), the combined organic extracts dried over magnesium sulphate and the solvent removed under reduced pressure. The crude product was chromatographed over silica eluting with a mixture of methanol and ethyl acetate (1:9) yielding the title compound as a pale red oil 3.5 g (40%).

N.m.r. (CDCl$_3$) 1.02 (t, J=6Hz, 3H); 1.28 (t, J=6Hz, 3H); 1.46 (d, J=6Hz, 3H); 1.78 (q, J=6Hz, 2H); 2.68 (m,

2H); 3.40 (s, 2H); 3.68 (m, 2H); 4.08 (s, 2H); 4.17 (q, J=6Hz, 2H); 4.43 (m, 1H); 6.92 and 6.98 (2 x s, 2H).

PREPARATION 4

Ethyl 4-[2-(2-methylbenzimidazol-1-yl)-2-methylpropoxy]-3-ketobutanoate

This compound was prepared following the procedure of Preparation 3 above using 2-(2-methylbenzimidazol-1-yl)-2-methylpropanol and ethyl-4-chloroacetoacetate.

N.m.r. (CDCl₃) 1.24 (t, J=6Hz, 3H); 1.95 (s, 6H); 2.83 (s, 3H); 3.30 (s, 2H); 3.97 (s, 2H); 4.03 (s, 2H); 4.16 (q, J=6Hz, 2H); 7.20 (m, 2H); 7.59 (d, J =8Hz, 1H); 7.70 (d, J=8Hz, 1H).

We claim:

1. A compound of the formula

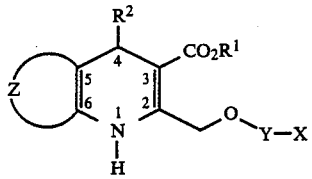

or a pharmaceutically acceptable salt thereof, wherein R¹ is alkyl having one to three carbon atoms; R² is 2-chlorophenyl; Y is alkylene having two to five carbon atoms with at least two carbon atoms in the chain linking X to the oxygen atom; X is 2-alkylimidazol-1-yl said alkyl having one to four carbon atoms, 2,4,5-trimethylimidazol-1-yl or 2-methylbenzimidazol-1-yl; and Z is

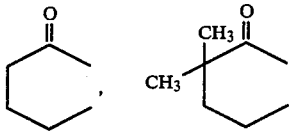

2. A compound of claim 1, wherein R¹ is ethyl, R² is 2-chlorophenyl and Y is ethylene.

3. The compound of claim 2, wherein X is 2-methylbenzimidazol-1-yl and Z is

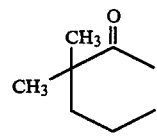

4. A pharmaceutical composition for treating an inflammatory or allergic comprising a unit dosage reaction in a mammal form of a compound according to claim 1 together with a pharmaceutically acceptable diluent or carrier.

5. A method for treating an inflammatory or allergic reaction in a mammal which comprises administering to said mammal an antiinflammatory or antiallergic effective amount of a compound according to claim 1.

* * * * *